United States Patent [19]

Rao

[11] Patent Number: 4,766,372
[45] Date of Patent: Aug. 23, 1988

[54] ELECTRON BEAM TESTER

[75] Inventor: Valluri R. M. Rao, Milpitas, Calif.

[73] Assignee: Intel Corporation, Santa Clara, Calif.

[21] Appl. No.: 13,006

[22] Filed: Feb. 10, 1987

[51] Int. Cl.$^4$ .................. G01N 23/00; H01J 37/26
[52] U.S. Cl. ...................... 324/158 R; 324/158 D;
                324/73 R; 250/396 ML; 250/310; 250/311
[58] Field of Search ............ 324/73 R, 158 R, 158 D;
                                250/310, 311, 397, 396 ML

[56]  References Cited
         U.S. PATENT DOCUMENTS

| | | | |
|---|---|---|---|
| 3,787,696 | 1/1974 | Dao et al. ........................ | 250/310 X |
| 3,961,190 | 6/1976 | Lukianoff et al. ............... | 250/310 X |
| 4,210,806 | 7/1980 | Broers ............................. | 250/397 X |
| 4,277,679 | 7/1981 | Feuerbaum ..................... | 324/158 DX |
| 4,442,355 | 4/1984 | Tamura et al. .................. | 250/310 X |
| 4,516,026 | 5/1985 | Jouffrey et al. ................. | 250/310 X |
| 4,675,524 | 6/1987 | Frosien et al. .................. | 250/311 X |

OTHER PUBLICATIONS

Plow et al.; "Operational Testing of L.S.I. Arrays by Stroposcopic Scanning Electron Microscopy,"; Microelectronics and Reliability; vol. 10, 1971; pp. 317–323.
Wolfgang; "Electron Beam Techniques for Microcircuit Inspection"; Microcircuit Engineering; 1980; pp. 409–438.
Menzel et al.; "Fundamentals of Electron beam Testing of Integrated Circuits"; Scanning vol. 5; 1983; pp. 103–122.
Brunner et al.; "Surface Potential Measurements on Floating Targets with a Parallel Beam Technique"; Journal of Vacuum Science Technology A; Oct./Dec. 1983; pp. 1–4.
Menzel et al.; "Secondary Electron Analyzes for Voltage Measurements; Scanning Electron Microscope; 1983; pp. 65–75.
Menzel et al.; "Characterization and Performance Improvement of Secondary Electron Analyzes"; J. Vac. Sci. Technol. B1(4); Oct.-Dec. 1983; pp. 1348–1351.
May et al.; "Dynamic Fault Imaging of VLSI Random Logic Devices"; IEEE/IRPS Transaction 1984; pp. 95–108.

Primary Examiner—Reinhard J. Eisenzopf
Assistant Examiner—Vinh P. Nguyen
Attorney, Agent, or Firm—Blakely, Sokoloff, Taylor & Zafman

[57]  ABSTRACT

An electron beam tester for fault detection and isolation in large and very large scale integrated circuits. An electron optical column focuses a primary beam of electrons on the surface of a circuit chip. An immersion extractor provides an electrical field to attract secondary electrons emitted from the irradiated surface. Secondary electrons are detected in an integral spectrometer. A wide bore final lens and integral high resolution double defection scan coils enable large area voltage contrast imaging as well as quantitative waveform measurement from internal nodes of the circuit chip.

30 Claims, 3 Drawing Sheets

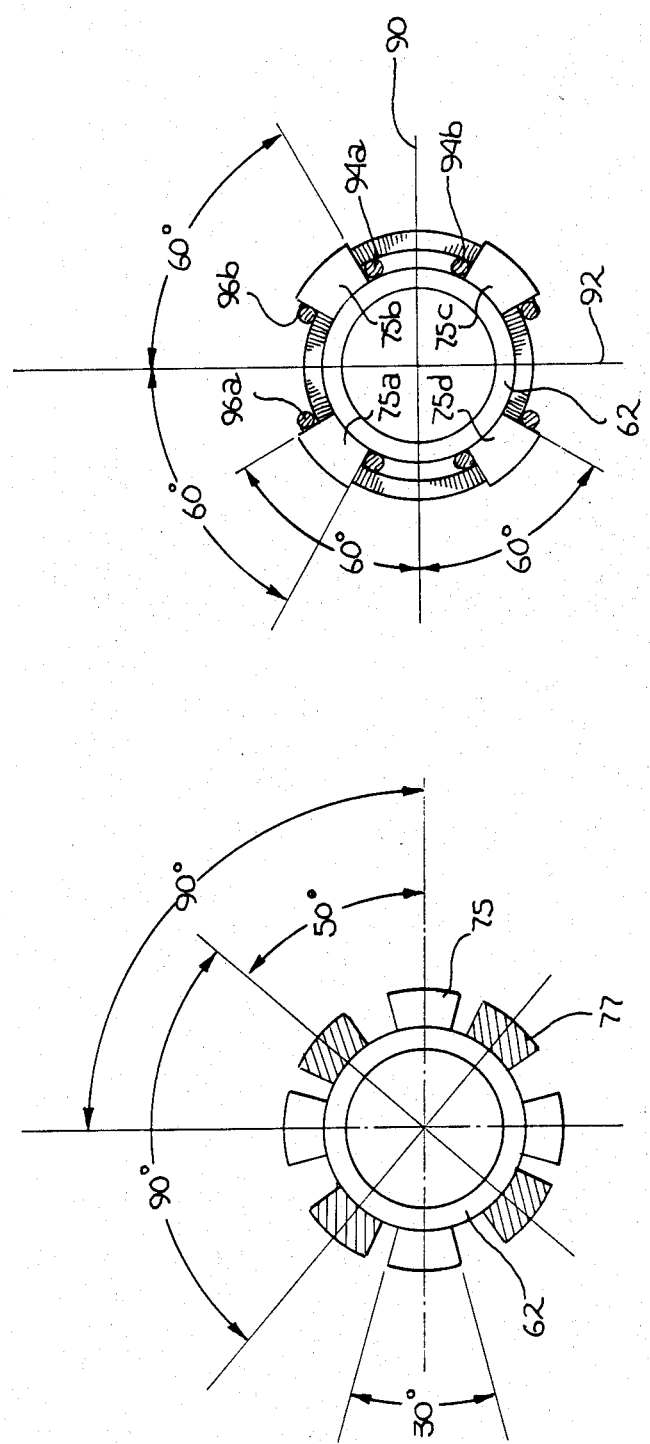

ELECTRON BEAM TESTER

BACKGROUND

1. Field of Invention

This invention relates generally to the field of electron beam circuit testers and particularly to apparatus adapted for testing large and very large scale integrated circuits.

2. Description of the Prior Art

As integrated circuits have become increasingly complex, traditional testing methods which involve the use of a mechanical probe to make electrical measurements on the surface of a circuit chip are no longer practical. Electron beam (e-beam) testing has become a practical alternative for testing large scale integrated circuits. Such testing equipment and techniques are described generally in E. Menzel and E. Kubalek, "Fundamentals of Electron Beam Testing of Integrated Circuits," *Scanning*, Vol. 5, pp. 103-122 (1983).

E-beam testing methods permit quantitative measurements of voltage waveforms from particular conductor paths of an integrated circuit to be obtained. In the typical test apparatus, a primary beam of electrons is focused on the point of interest on the surface of a specimen chip. Secondary electrons which are emitted in response to the impinging primary beam have an energy distribution which depends on the local surface conditions. The characteristic energy spectrum of the secondary electrons exhibits an energy shift as a voltage is applied to the irradiated portion of the specimen. The secondary electron energy spectrum can thus be analyzed to yield a measure of voltage at the surface of the chip analogous to that which would be obtained with a conventional probe applied to the circuit specimen. A spectrometer to perform such energy analysis is typically retrofitted to a conventional scanning electron microscope (SEM).

An alternative test method employs qualitative voltage contrast. In this technique, an image of an area of the specimen chip is obtained. Due to retarding electrical fields in the vicinity of positively biased regions of the chip surface, fewer secondary electrons will escape from these regions and they will therefore appear darker in the image. Conversely, regions of the chip surface with a negative electrical bias will appear brighter. Such images may be obtained with conventional SEMs.

Dynamic testing of circuits is facilitated by stroboscopic operation of the e-beam tester in synchronism with the operation of the device under test. Images and/or voltage measurements can thus be obtained at points in time corresponding to known logic states of the device.

Conventional SEMs have a relatively limited field of view. Systems with wider fields of view are hampered by distortion and loss of resolution towards the edge of the image. Consequently, voltage contrast imaging is difficult to accomplish over a significant portion of the surface of an integrated circuit without physically repositioning the specimen.

The imaging capability of systems adapted for quantitative waveform measurement is further hampered by the incorporation of an energy analyzer which impairs the field of view.

In addition, the distortions and aberrations of a conventional SEM make accurate beam positioning difficult. Highly accurate beam positioning is desirable so that the e-beam can be positioned on the surface of a specimen chip in response to positioning commands derived from information stored in computer aided design (CAD) systems.

Consequently, there is a need for an e-beam integrated circuit tester which offers a wide field of view within which the e-beam can be accurately positioned and which also incorporates an integral energy analyzer for performing quantitative waveform measurement.

BRIEF SUMMARY OF THE INVENTION

The apparatus of the present invention combines a wide field of view lens, high resolution deflection system, and integral spectrometer so that both wide field voltage contrast imaging and quantitative waveform measurement may be performed.

A final lens comprises a large bore cylindrical upper pole piece of ferrite surrounding a glass liner tube. An annular lower pole piece of low carbon iron is positioned so as to define a 1 mm gap. The pole pieces are configured such that the peak magnetic field of the lens coincides with a plane approximately 10 mm below the optical center of the lens, at which plane the surface of the specimen chip is preferably positioned. The lens is energized by means of a 700 turn coil.

Concentric with and wholly within the ferrite pole piece is a set of high resolution double deflection scanning coils. Each individual coil defines a 120° saddle adjacent to the exterior of the glass liner tube. Windings of the overlapping X-axis and Y-axis coils are interleaved. An upper set of coils is rotated by 50° with respect to a lower set of coils. The upper and lower sets of coils are similarly configured except that each upper coil comprises 5 turns whereas each lower coil comprises 20 turns.

The interior surface of the glass liner tube is coated with a 25 micron conductive layer of iron oxide to which an extraction potential of approximately 400 to 600 volts is applied. The energized tube in combination with a grounded plate immediately below the lower pole piece forms an immersion extractor to accelerate secondary electrons from the surface of the specimen under test upwards toward an integral spectrometer located immediately above the lens.

The spectrometer comprises a series of conductive rings concentric with the bore of the tester to which stepped retarding potentials are applied. It further comprises dual retarding grids and an exit grid on which a potential of approximately 30 volts is impressed. Secondary electrons which have been decelerated by the retarding fields are captured by the exit grid and strike the surface of a scintillator which is optically coupled to a photomultiplier. Quantitative voltage measurements are performed by regulating the potential applied to the retarding grids so as to maintain a constant output at the photomultiplier.

BRIEF DESCRIPTION OF THE DRAWINGS

FIGS. 3a—3b illustrate the detailed construction of the scan coils of the preferred embodiment.

DETAILED DESCRIPTION OF THE PREFERRED EMBODIMENT

While the invention is herein described in terms of a preferred embodiment, it will be understood by those skilled in the art that numerous variations in form and detail may be made within the teachings or the present disclosure. Accordingly, it is to be understood that the terminology used is for the purpose of description rather than limitation.

Figure 1:
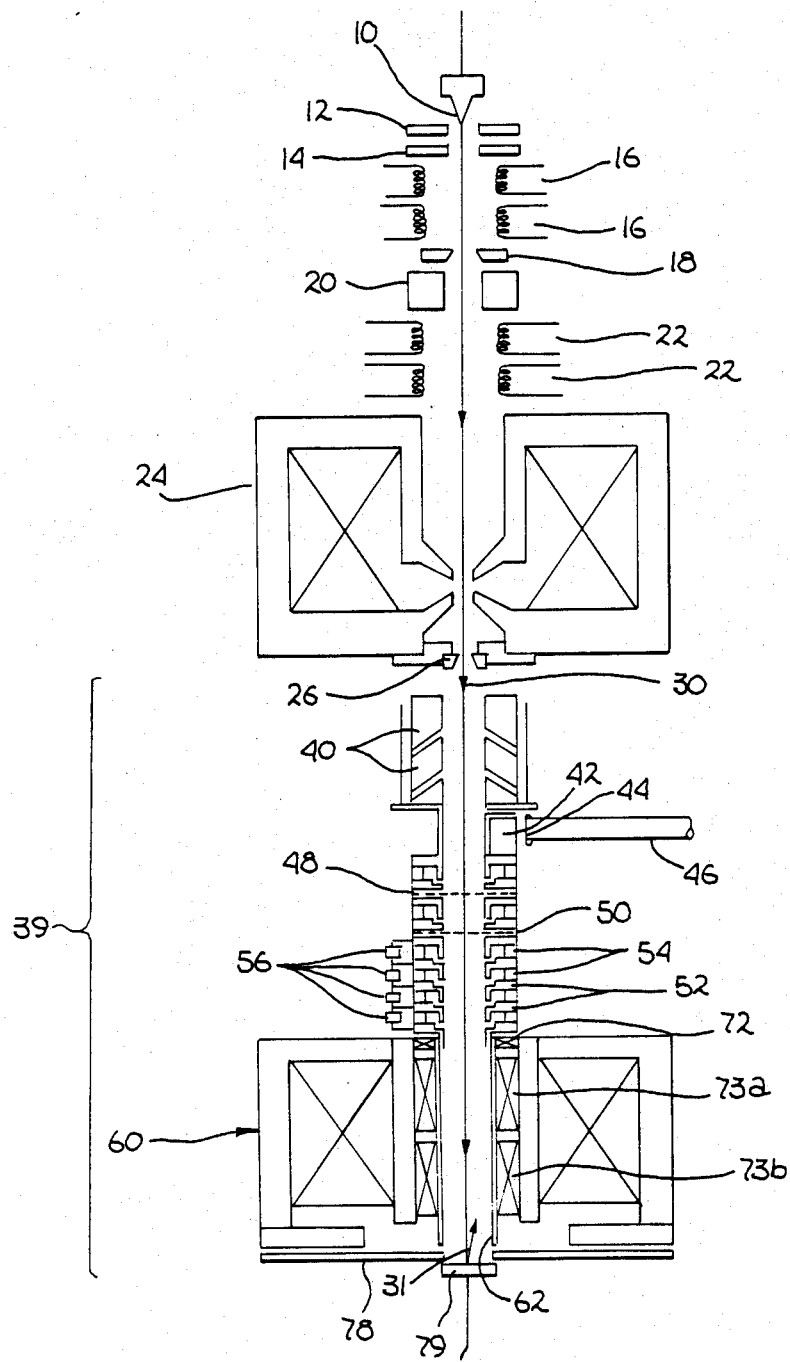
FIG. 1 is a schematic cross section of an apparatus of the present invention shown in conjunction with elements of a conventional electron microscope.

FIG. 1 schematically illustrates the present invention as it relates to conventional elements of a scanning electron microscope (SEM) which are well known in the art. An electron source, such as filament 10, emits free electrons in response to an electrical current which is applied thereto. The electrons are accelerated by means of electrical potentials applied to wehnelt 12 and anode 14. Initial beam alignment is performed by magnetic double alignment coils 16. The electron beam then passes through beam defining aperture 18, which in the preferred embodiment is approximately 50 microns in diameter. The electron beam next passes between beam blanking plates 20 to which a sufficient electrical potential may be applied to deflect substantially all of the electrons in the beam away from the optical axis, thereby effectively acting as a shutter to facilitate stroboscopic testing of a specimen circuit. In the preferred embodiment, beam blanking plates 20 are cylindrical sections approximately 5 millimeters long with a bore of approximately 3 millimeters. The unblanked electron beam next passes through a second set of magnetic double alignment coils 22. The electron beam emerging from alignment coils 22 is focused by condenser lens 24. In the preferred embodiment, this lens provides a demagnification factor of approximately 10. Electron beam 30 emerges from final aperture 26. This aperture perferably has a diameter of a few hundred microns.

The components thus far described will be recognized by persons skilled in the art as common to electron microscopes generally. It is to be understood that configurations of components other than that described herein may be equally well suited for providing a beam of primary electrons with which the present invention may be employed.

Primary electron beam 30 which exits final aperture 26 enters lower section 39 having a generally cylindrical bore. Double electrostatic deflectors 40 deflect primary electron beam 30 by an amount sufficient to cancel the beam deflection which is caused by exit grid 42 whose function with respect to secondary electrons will be described below. Retarding grids 48,50 have central apertures which permit primary electron beam 30 to pass through without obstruction. Primary electron beam 30 next passes within conductive rings 52 which establish a potential gradient for interaction with secondary electrons.

Circularlity of primary electron beam 30 is improved by stigmator 72. Stigmator 72 comprises 8 coils, shown as reference number 72a in FIG. 2, radially disposed about the circumference of cylindrical liner tube 62. The coils are arranged in two sets of 4 coils each, the coils within each set positioned at 90° intervals and displaced 45° with respect to the other set. Diametrically opposite coils within each set are wound in opposition. The function of stigmator 72 with respect to the electron beam is analogous to that of an optical cylindrical lens for correcting astigmatism in a beam of light. Details of the contruction of stigmator 72 are well known to those skilled in the art of electron beam devices.

Final demagnification of primary electron beam 30 is performed by final lens 60. Scan coils 73a, 73b are concentric with and disposed within the bore of final lens 60 and permit deflection of primary electron beam 30 in two orthogonal axes perpendicular to the optical axis of the lens. Scan coils 73a, 73b are energized such that primary electron beam 30 is positioned to irradiate a desired node of specimen chip 79 for obtaining either quantitative or qualitative waveform measurements. Alternatively, scan coils 73a, 73b may be energized with time varying currents such that primary electron beam 30 scans the surface of specimen 79 in a predetermined pattern to obtain a conventional or voltage contrast image.

Primary electrons striking the surface of specimen 79 cause the emission of secondary electrons 31. The interior surface of liner tube 62 is coated with a conductive material such as a 25 micron layer of iron oxide as used in the preferred embodiment. An electrical potential applied to the conductive coating in liner tube 62 in combination with grounded conductive plate 78 creates an immersion extractor that accelerates secondary electrons 31 away from the surface of specimen 79. In the preferred embodiment, an extraction potential of approximately 400 to 600 volts is applied to the inner surface of liner tube 62. The immersion extractor design, which is well-known in the art, was chosen for the preferred embodiment to avoid the hazard of having a high voltage in close proximity to the specimen under test that is present when a planar extraction grid design is employed.

Conductive rings 52 are separated by insulating rings 54 and are electrically connected to resistors 56. Resistors 56 are electrically connected to a voltage source (not shown). Resistors 56 comprise a resistive divider network such that a stepped potential gradient intermediate to the extraction potential and retarding grid potential is applied to the internal cylindrical surface formed by conductive rings 52 above liner tube 62 and below retarding grid 50. Secondary electrons 31 are decelerated by the stepped potential gradient applied to rings 52 and by electrical potentials applied to retarding grids 48, 50. Decelerated secondary electrons are captured by exit grid 42 which is positioned to the side of the bore of upper section 39 and strike the surface of scintillator 44. Light produced by scintillator 44 in response to secondary electrons is conducted by light pipe 46 to a photomultiplier (not shown). The potential applied to retarding grids 48, 50 may be controlled by electronic circuitry (not shown) so as to maintain a constant output at the photomultiplier thereby obtaining a measure of the energy distribution of secondary electrons 31.

Lower section 39 thus comprises a wide bore focusing lens, high-resolution scan deflector and secondary electron energy analyzer integrally associated in a single assembly. This design allows the present invention to perform both wide field of view voltage contrast imaging and quantitative waveform measurement.

Details of the construction of lens 60 and scan coils 73a, 73b will now be described. While the following description is specific, it will be understood by those skilled in the art that variations in configurations and dimensions of components may be made within the teachings of the present disclosure. It is to be understood that the optical properties of lens 60 and scan coils 73a, 73b have been optimized in the preferred embodiment for operation at a low accelerating voltage of up to approximately 3 Kev. This is accomplished by minimization of the chromatic aberration of focus and deflection.

Figure 2:
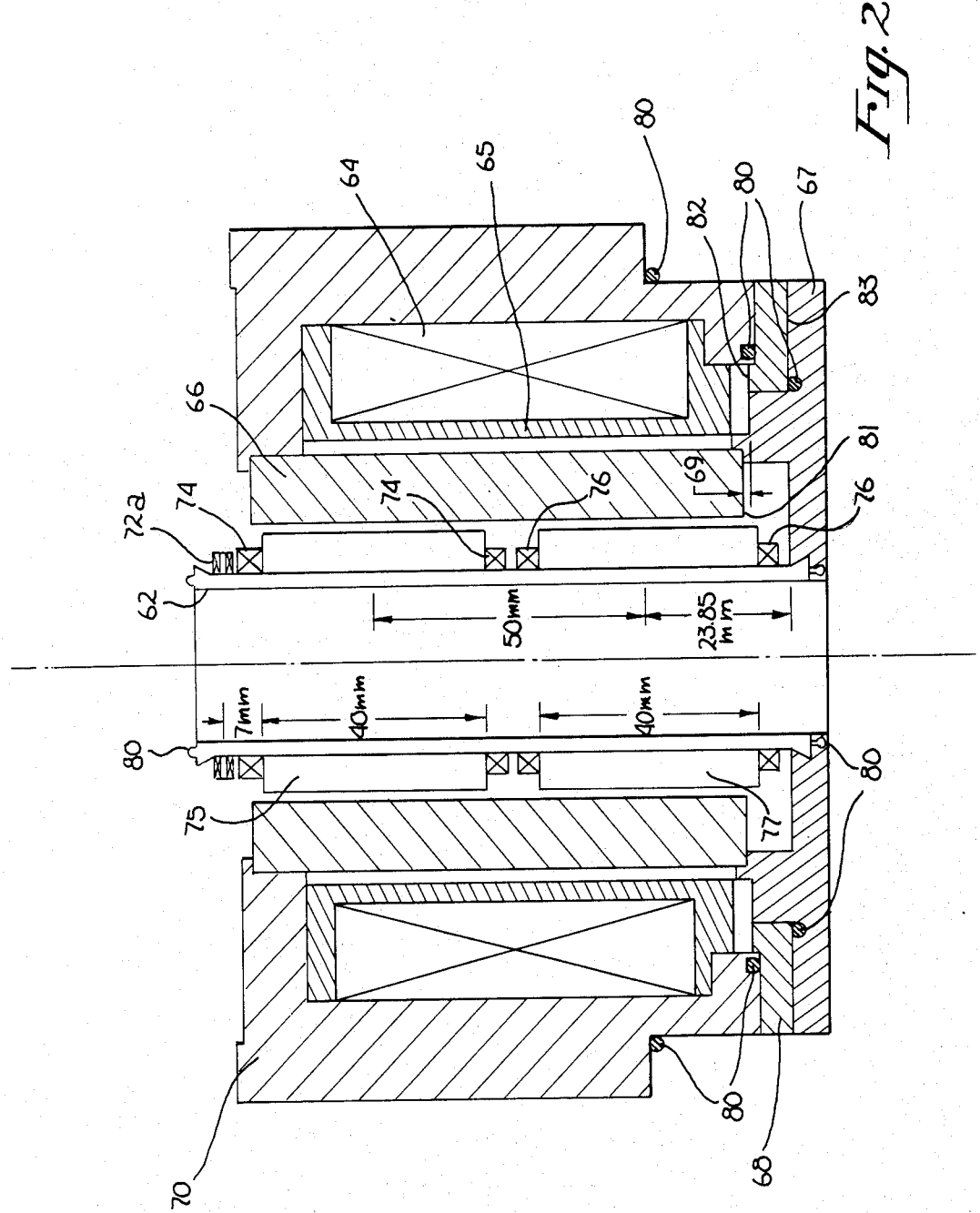
FIG. 2 is a detailed cross section of the final lens and scan coils of the apparatus of FIG. 1.

Details of final lens 60 and scan coils 73a, 73b are more fully shown in FIG. 2. Lens 60 comprises upper pole piece 66, spacer 67, lower pole piece 68, magnetic circuit 70, coil former 65 and lens coil 64. Lens coil 64 is wound about cylindrical coil former 65 which is made of a non-magnetic material. In the preferred embodiment, coil former 65 is aluminum alloy and lens coil 64 comprises 700 turns. Upper pole piece 66 consists of a cylinder of solid ferrite with a bore of 50 millimeters and a wall thickness of 12.5 millimeters. Lower pole piece 68 is an annular ring of low carbon iron with a bore of 94 millimeters and a thickness of 7 millimeters. Pole pieces 66, 68 are connected by magnetic circuit 70 which comprises a cylinder of low carbon iron. Pole pieces 66, 68 are held in position by spacer 67. Spacer 67 consists of a non magnetic material, preferably aluminum alloy, and is machined such that lower surface 81 of upper pole piece 66 is positioned relative to upper surface 82 of lower pole piece 68 so as to define gap 69. In the preferred embodiment, gap 69 is approximately 1 millimeter. Final lens 60 as thus constructed produces a maximum flux density, which is axially displaced below the optical center of lens 60. In the preferred embodiment, a maximum flux density of approximately 14 MTeslas is achieved at a plane approximately 10 millimeters below the optical center of lens 60 using a lens excitation of 793 ampere turns. The surface of the specimen chip is preferrably placed at this plane.

Liner tube 62 forms a portion of a pressure vessel in which a vacuum is maintained. It is preferrably made of ceramic, although glass, as used in the preferred embodiment is also suitable. Pressure containment is acheived by means of O-rings 80.

Upper scan coil 73a and lower scan coil 73b are formed adjacent to the exterior surface of liner tube 62 and disposed concentrically within the bore of upper pole piece 66. Upper scan coil 73a comprises coil formers 75 and coil windings 74 as shown in FIG. 2. Similarly, lower scan coil 73b comprises coil formers 77 and coil windings 76. The coils are constructed such that diametrically opposed coils define X scan axis 90 and Y scan axis 92 as shown in FIG. 3b. Upper scan coil 74 is wound around coil formers 75 and lower scan coil 76 is wound around coil formers 77. Coil formers 75, 77 consist of a rigid insulating material affixed to the outer surface of liner tube 62. The formers are preferrably made of ceramic or glass, however, a plastic material such as Delrin is also suitable. As shown in FIG. 3a, upper coil formers 75 each have a circumferential extent of 30° and are spaced at 90° intervals about the circumference of liner tube 62. Lower coil formers 77 are identically disposed but are rotated about the circumference of liner tube 62 by 50° counterclockwise when looking toward the specimen with respect to upper coil formers 75. All coil formers have a length of 40 millimeters measured with respect to the axis of liner tube 62. Lower coil formers 77 are axially located such that the coil centers are 23.85 millimeters above lower surface 83 of lower pole piece 67. Upper coil formers 75 are axially located such that they are centered 50 millimeters above lower coil formers 77.

Details of the scan coil construction are shown in FIG. 3b. One turn of Y-axis coil 94a is wound around coil formers 75a and 75b and one turn of Y-axis coil 94b is wound around coil formers 75c and 75d. Next, one turn of X-axis coil 96a is wound around coil formers 75a and 75d and one turn of X-axis coil 96b is wound around coil formers 75b and 75c. When winding an odd number of turns, successive turns of the Y and X-axis coils are interleaved in a similar fashion. When winding an even number of turns, pairs of turns are interleaved except for the first and last turn. For example, a four turn coil would be wound in the sequence: Y, X, X, Y, Y, X, X, Y. This sequence assures that the deflection centers of the X and Y scan axes are coincident.

In the preferred embodiment, upper scan coil 74 comprises 5 turns per coil and lower scan coil 76 comprises twenty turns per coil. Although FIG. 3b illustrates the winding strategy for upper scan coil 74, the identical strategy is employed for lower scan coil 76. Each scan coil set therefore comprises two pairs of diametrically opposed 120° saddle coils. In the preferred embodiment scan coils 74, 76 are wound with 24 gauge enamelled copper wire.

The scan coils as thus constructed permit extremely accurate positioning of the primary electron beam throughout the field of view such that quantitative waveform measurements of circuit nodes may be obtained over a broad area of a specimen chip. Furthermore, the positioning accuracy lends itself to interactive operation with Computer Aided Design systems which may provide beam positioning commands.

I claim:

1. An apparatus for testing integrated circuits comprising:
    electron emitting means for providing a plurality of primary electrons;
    accelerating means operatively associated with the electron emitting means for accelerating the primary electrons along a substantially linear path;
    alignment means operatively associated with the accelerating means for aligning the path of the primary electrons with an optical axis;
    first lens means operatively associated with the alignment means for focusing the primary electrons into a beam directed along the optical axis;
    second lens means operatively associated with the first lens means for focusing the beam of primary electrons on a surface of a specimen such that a plurality of secondary electrons is emitted from the surface of the specimen;
    deflection means operatively associated with the second lens means for selectively positioning the beam of primary electrons on the surface of the specimen;
    extraction means operatively associated with the second lens means for accelerating the secondary electrons in a direction along the optical axis and substantially opposite to the direction of the beam of primary electrons;
    retarding means operatively associated with the extraction means for controllably decelerating the secondary electrons; and
    detection means operatively associated with the retarding means for providing an electrical signal as a function of a potential of the secondary electrons;
    whereby said electrical signal varies as a function of a surface potential at a location on the surface of the specimen where the beam of primary electrons is positioned.

2. The apparatus of claim 1 wherein the retarding means is disposed ahead of the second lens means with respect to the direction of the beam of primary electrons.

3. The apparatus of claim 2 wherein wherein the retarding means comprises a plurality of annular conductive rings disposed coaxially with the optical axis and at least one conductive grid in a plane perpendicular to the optical axis.

4. The apparatus of claim 3 wherein the annular conductive rings are electrically energized by the respective outputs of a plurality of resistors arranged in a divider network, one of which resistors is electrically connected to a voltage source, whereby a stepped potential gradient is impressed on the interior cylindrical surface defined by the annular conductive rings.

5. The apparatus of claim 1 wherein the second lens means comprises a cylindrical pole piece.

6. The apparatus of claim 5 wherein the deflection means is disposed within the interior of the cylindrical pole piece.

7. The apparatus of claim 3 wherein the cylindrical pole piece has an interior diameter of at least 50 millimeters.

8. The apparatus of claim 3 wherein the cylindrical pole piece is made of ferrite.

9. The apparatus of claim 1 wherein the deflection means comprises a first pair of upper scan coils for deflecting the beam of primary electrons in a first direction perpendicular to the optical axis, a second pair of upper scan coils for deflecting the beam of primary electrons in a second direction perpendicular to the optical axis and orthogonal to the first direction, a first pair of lower scan coils for deflecting the beam of primary electrons in a third direction perpendicular to the optical axis and having an angle of orientation with respect to the first direction, and a second pair of lower scan coils for deflecting the beam of primary electrons in a fourth direction perpendicular to the optical axis and orthogonal to the third direction.

10. The apparatus of claim 9 wherein the angle of orientation is 50 degrees.

11. The apparatus of claim 9 wherein the first and second pair of upper scan coils and the first and second pair of lower scan coils each comprises two coils on diametrically opposite sides of the optical axis, each coil defining a cylindrical saddle whose axis is coincident with the optical axis.

12. The apparatus of claim 1 wherein the deflection means comprises a pair of X scan coils for deflecting the beam of primary electrons in a first direction perpendicular to the optical axis and a pair of Y scan coils for deflecting the beam of primary electrons in a second direction perpendicular to the optical axis and orthogonal to the first direction, each of said pairs of scan coils comprising an equal even number N of turns of conductive wire, each turn of each coil overlapping turns of both coils of the alternate pair in a general sequence of:

$Y_1, X_1, X_2, Y_2, Y_3, X_3, X_4, \ldots, Y_{N-2}, Y_{N-1}, X_{N-1}, X_N, Y_N$;

whereby an X deflection center of the X scan coils is coincident with a Y deflection center of the Y scan coils.

13. An apparatus for testing integrated circuits comprising:
source means for providing a focused beam of primary electrons directed along an optical axis;
lens means operatively associated with the source means for focusing the beam of primary electrons on a surface of a specimen such that a plurality of secondary electrons is emitted from the surface of the specimen, said lens means comprising a cylindrical pole piece whose axis is coincident with the optical axis;
extraction means for accelerating the secondary electrons in a direction along the optical axis and substantially opposite to the direction of the beam of primary electrons comprising a cylindrical liner tube disposed within the cylindrical pole piece and having a conductive inner surface to which an electrical potential is applied and an electrically grounded conductive plate lying in a plane perpendicular to the optical axis and disposed at an end of the cylindrical liner tube from which the beam of primary electrons exits;
deflection means for selectively positioning the beam of primary electrons on the surface of the specimen comprising a plurality of scan coils disposed between the interior surface of the cylindrical pole piece and exterior surface of the cylindrical liner tube;
retarding means for controllably decelerating the secondary electrons comprising a plurality of annular conductive rings disposed coaxially with the optical axis at an end of the cylindrical liner tube in which the beam of primary electrons enters and at least one conductive grid in a plane perpendicular to the optical axis; and
detection means operatively associated with the retarding means for providing an electrical signal as a function of a potential of the secondary electrons;
whereby said electrical signal varies as a function of a surface potential at a location on the surface of the specimen where the beam of primary electrons is positioned.

14. The apparatus of claim 13 wherein the cylindrical pole piece has an interior diameter of at least 50 millimeters.

15. The apparatus of claim 13 wherein the cylindrical pole piece is made of ferrite.

16. The apparatus of claim 13 wherein the deflection means comprises a first pair of upper scan coils for deflecting the beam of primary electrons in a first direction perpendicular to the optical axis, a second pair of upper scan coils for deflecting the beam of primary electrons in a second direction perpendicular to the optical axis and orthogonal to the first direction, a first pair of lower scan coils for deflecting the beam of primary electrons in a third direction perpendicular to the optical axis and having an angle of orientation with respect to the first direction, and a second pair of lower scan coils for deflecting the beam of primary electrons in a fourth direction perpendicular to the optical axis and orthogonal to the third direction.

17. The apparatus of claim 16 wherein the angle of orientation is 50 degrees.

18. The apparatus of claim 16 wherein the first and second pair of upper scan coils and the first and second pair of lower scan coils each comprises two coils on diametrically opposite sides of the optical axis, each coil defining a cylindrical saddle whose axis is coincident with the optical axis.

19. The apparatus of claim 13 wherein the deflection means comprises a pair of X scan coils for deflecting the beam of primary electrons in a first direction perpendicular to the optical axis and a pair of Y scan coils for deflecting the beam of primary electrons in a second direction perpendicular to the optical axis and orthogonal to the first direction, each of said pairs of scan coils comprising an equal even number N of turns of conductive wire, each turn of each coil overlapping turns of both coils of the alternate pair in a general sequence of:

$Y_1, X_1, X_2, Y_2, Y_3, X_3, X_4, \ldots, Y_{N-2}, Y_{N-1}, X_{N-1}, X_N, Y_N$;

whereby an X deflection center of the X scan coils is coincident with a Y deflection center of the Y scan coils.

20. An improved electron beam circuit testing apparatus of the type having a beam of primary electrons which is incident upon a surface of a circuit specimen, said surface emitting a plurality of secondary electrons in response to the beam of primary electrons, and having extraction means for accelerating the secondary electrons away from said surface, wherein the improvement comprises:

a final lens having a generally toroidal winding;

deflection means disposed within said generally toroidal winding of said final lens for selectively positioning the beam of primary electrons on the surface of the specimen;

retarding means disposed ahead of the final lens with respect to the direction of the beam of primary electrons for controllably decelerating the secondary electrons; and detection means operatively associated with the retarding means for providing an electrical signal as a function of a potential of the secondary electrons;

whereby said electrical signal varies as a function of a surface potential at a location on the surface of the specimen where the beam of primary electrons is positioned.

21. The improved apparatus of claim 20 wherein the final lens comprises a cylindrical pole piece.

22. The improved apparatus of claim 21 wherein the cylindrical pole piece has an interior diameter of at least 50 millimeters.

23. The improved apparatus of claim 21 wherein the cylindrical pole piece is made of ferrite.

24. The improved apparatus of claim 20 wherein the deflection means comprises a first pair of upper scan coils for deflecting the beam of primary electrons in a first direction perpendicular to the optical axis, a second pair of upper scan coils for deflecting the beam of primary electrons in a second direction perpendicular to the optical axis and orthogonal to the first direction, a first pair of lower scan coils for deflecting the beam of primary electrons in a third direction perpendicular to the optical axis and having an angle of orientation with respect to the first direction, and a second pair of lower scan coils for deflecting the beam of primary electrons in a fourth direction perpendicular to the optical axis and orthogonal to the third direction.

25. The improved apparatus of claim 24 wherein the angle of orientation is 50 degrees.

26. The improved apparatus of claim 24 wherein the first and second pair of upper scan coils and the first and second pair of lower scan coils each comprises two coils on diametrically opposite sides of the optical axis, each coil defining a cylindrical saddle whose axis is coincident with the optical axis.

27. The improved apparatus of claim 24 wherein the first and second pair of upper scan coils and first and second pair of lower scan coils are disposed within a cylindrical pole piece of the final lens.

28. The improved apparatus of claim 20 wherein the retarding means comprises a plurality of annular conductive rings disposed coaxially with the optical axis and at least one conductive grid in a plane perpendicular to the optical axis.

29. The improved apparatus of claim 28 wherein the annular conductive rings are electrically energized by the respective outputs of a plurality of resistors arranged in a divider network, one of which resistors is electrically connected to a voltage source, whereby a stepped potential gradient is impressed on the interior cylindrical surface defined by the annular conductive rings.

30. The apparatus of claim 20 wherein the deflection means comprises a pair of X scan coils for deflecting the beam of primary electrons in a first direction perpendicular to the optical axis and a pair of Y scan coils for deflecting the beam of primary electrons in a second direction perpendicular to the optical axis and orthogonal to the first direction, each of said pairs of scan coils comprising an equal even number N of turns of conductive wire, each turn of each coil overlapping turns of both coils of the alternate pair in a general sequence of:

$Y_1, X_1, X_2, Y_2, Y_3, X_3, X_4, \ldots, Y_{N-2}, Y_{N-1}, X_{N-1}, X_N, Y_N$;

whereby an X deflection center of the X scan coils is coincident with a Y deflection center of the Y scan coils.

* * * * *